(12) United States Patent
Kaercher et al.

(10) Patent No.: US 9,579,089 B2
(45) Date of Patent: Feb. 28, 2017

(54) MANIPULATION DEVICE FOR A MEDICAL INSTRUMENT

(71) Applicant: Karl Storz GmbH & Co. KG, Tuttlingen (DE)

(72) Inventors: Daniel Kaercher, Radolfzell (DE); Jochen Stefan, Wald (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 921 days.

(21) Appl. No.: 13/864,939

(22) Filed: Apr. 17, 2013

(65) Prior Publication Data

US 2013/0310813 A1 Nov. 21, 2013

(30) Foreign Application Priority Data

Apr. 18, 2012 (DE) ........................ 10 2012 007 649

(51) Int. Cl.
*A61B 17/00* (2006.01)
*A61B 19/00* (2006.01)
*A61B 17/29* (2006.01)

(52) U.S. Cl.
CPC ........ *A61B 17/00234* (2013.01); *A61B 17/00* (2013.01); *A61B 17/2909* (2013.01); *A61B 34/70* (2016.02); *A61B 2017/0046* (2013.01); *A61B 2017/00477* (2013.01); *A61B 2017/2919* (2013.01); *Y10T 403/59* (2015.01)

(58) Field of Classification Search
CPC .............. A61B 17/00234; A61B 17/00; A61B 17/2909; A61B 19/22; A61B 34/70
See application file for complete search history.

(56) References Cited

U.S. PATENT DOCUMENTS

| 5,505,737 A | 4/1996 | Gosselin et al. |
|---|---|---|
| 6,139,214 A | 10/2000 | Zirps et al. |
| 2009/0069842 A1 | 3/2009 | Lee et al. |
| 2009/0171147 A1 | 7/2009 | Lee et al. |

FOREIGN PATENT DOCUMENTS

| DE | 19722062 A1 | 12/1998 |
|---|---|---|
| DE | 10236274 A1 | 3/2004 |
| DE | 10357105 B3 | 4/2005 |
| DE | 102004049243 A1 | 4/2006 |
| WO | 2010045701 A1 | 4/2010 |

*Primary Examiner* — Ashley Fishback
(74) *Attorney, Agent, or Firm* — Whitmyer IP Group LLC (57) ABSTRACT

A manipulation device for mechanical connection with connection with the proximal end of a shaft, for forming a medical instrument, includes a plurality of retaining devices, wherein each one of the plurality of retaining devices is designed to releasably retain the proximal end of a shaft or the proximal end of a transmission device for transmitting at least either a force or a torque in the shaft, a manually activatable actuation device, and a coupling device for mechanically coupling the actuation device to the plurality of retaining devices, in such a way that a manual activation of the actuation device causes a release of the plurality of retaining devices.

12 Claims, 3 Drawing Sheets

MANIPULATION DEVICE FOR A MEDICAL INSTRUMENT

FIELD OF THE INVENTION

The present invention relates to a manipulation device for mechanical connection with connection with the proximal end of a shaft, for forming a medical instrument, and to a medical instrument with such a manipulation device.

BACKGROUND OF THE INVENTION

The expectations placed on medical instruments for micro-invasive procedures are constantly increasing. Medical instruments having a tool with a grasping or cutting function at the distal end, where the tool is rotatable about the longitudinal axis of the shaft, are already widely available in many forms. The grasping or cutting function and the rotation of the tool can be controlled, for example, by a single transmission rod, which transmits longitudinal forces and torques. Moreover, in recent times, the shaft can be angled proximally of the tool, and, in order to control this angle, a second transmission element can be provided in the shaft of the medical instrument, for example a second transmission rod.

In the case of re-usable medical instruments, it is necessary that they should be able to be dismantled as far as possible for cleaning. In particular, in many medical instruments, the manipulation device is separable from the proximal end of the shaft. For example, a locking connection between the proximal end of the shaft or outer shaft, on the one hand, and the manipulation device, on the other hand, can be unlocked by applying manual pressure to an unlocking button or by activating another actuation device. In the case of medical instruments produced by the applicant and sold under the name "Clickline", when the shaft is pulled distally out of the manipulation device, the proximal end of the transmission rod, and a lever of the retaining device coupled thereto, reach positions in which they are no longer coupled to each other. The coupling between the proximal end of the transmission rod and the manipulation device, or a lever on the manipulation device, is therefore releasable when the coupling between the proximal end of the shaft and the manipulation device is released.

However, the releasability or separability of the proximal ends of the outer shaft and of the transmission rod, on the one hand, from the manipulation device, on the other hand, as known from "Clickline" products, cannot be transferred, or cannot be easily transferred, to many other medical instruments. An alternative is to provide a separate actuation device for each coupling. In the case of a medical instrument with an outer shaft and with two transmission rods or other transmission devices, three actuation devices therefore have to be provided, the manual activation of these actuation devices releasing a respective coupling between the proximal end of the outer shaft or of a transmission rod, on the one hand, and the manipulation device, on the other hand.

SUMMARY OF THE INVENTION

An object of the present invention is to make available an improved manipulation device for a medical instrument and to make available an improved medical instrument.

This object is achieved by the subject matter of the independent claims.

Developments are set forth in the dependent claims.

Illustrative embodiments of the present invention are based on the concept that, on a manipulation device, a plurality of retaining devices for releasably retaining in each case a proximal end of a shaft or of a transmission device of a medical instrument are coupled to an actuation device in such a way that, by manually activating the actuation device, all of the retaining devices can be released. A manipulation device that is so equipped can be completely separated from the shaft, and from one or more transmission devices of the shaft, in a single movement, and therefore particularly easily and quickly. The medical instrument can therefore be dismantled in a way that places much less demand on the medical personnel than would be the case if several actuation devices had to be activated simultaneously or in succession or even in a predetermined sequence. Thus, the risk of damage to the medical instrument through incorrect handling during dismantling is also reduced.

Illustrative embodiments of the present invention are also based on the concept that, on a manipulation device, a manually activatable actuation device is mechanically coupled to a movable retaining device, for releasably retaining the proximal end of a shaft or of a transmission device, in such a way that, independently of the relative position of retaining device and actuation device, an activation of the actuation device causes a release of the retaining device. After a medical instrument has been used, and before it is cleaned or reconfigured, this can facilitate separation of the manipulation device from a shaft, for example since a tool does not first of all have to be brought to a defined position. The amount of training required by personnel can therefore be reduced, and there is less risk of damage due to incorrect handling. Moreover, the time spent on dismantling a medical instrument can be reduced.

A manipulation device for mechanical connection with connection with the proximal end of a shaft, for forming a medical instrument, comprises a plurality of retaining devices, wherein each one of the plurality of retaining devices is designed to releasably retain the proximal end of a shaft or the proximal end of a transmission device for transmitting at least either a force or a torque in the shaft, a manually activatable actuation device, and a coupling device for mechanically coupling the actuation device to the plurality of retaining devices, in such a way that a manual activation of the actuation device causes a release of the plurality of retaining devices.

The manipulation device is in particular provided and designed to be mechanically connected in a releasable manner to a shaft which has, within an outer shaft, one or more transmission devices in the form of one or more transmission rods and/or in the form of an inner shaft. The one or more transmission devices are displaceable relative to one another and relative to the inner shaft in a direction parallel to the longitudinal axis of the outer shaft and, therefore, in particular also parallel to the longitudinal axes of the transmission devices and/or are rotatable about the longitudinal axis, in order in each case to permit the transfer of a force and/or of a torque to the distal end of the shaft. In particular, the manipulation device is designed for releasable mechanical connection with connection with an outer shaft, an inner shaft and a transmission rod, which are arranged coaxially.

Each retaining device is in particular designed to transfer forces to the proximal end of a transmission device, in a direction parallel to the longitudinal axis of the shaft and, therefore, in particular also in a direction parallel to the longitudinal axis of a transmission device. Each retaining device can also be designed to transfer a torque to the proximal end of the assigned shaft or to the proximal end of the assigned transmission device. For this purpose, the retaining device has in particular a recess for the proximal end of the shaft or of the transmission device, which recess has a cross section that is non-rotationally symmetrical and corresponds to the proximal end of the shaft or of the transmission device.

Each individual retaining device has in particular a retaining or closed or locked state, and a released or opened or unlocked state. In the retaining state, the retaining device can retain the proximal end of a shaft or of a transmission device or be mechanically connected to the proximal end, in particular with a form fit, a force fit or a friction fit. The retaining device can be designed to assume a state corresponding to the retaining state even in the absence of a proximal end of a shaft or of a transmission device. In the released state, a proximal end of a shaft or of a transmission device can be separated from the retaining device. The retaining device is in particular designed to receive a proximal end of a shaft or of a transmission device in the retaining device only in the released state. In this case, the retaining device can be designed to change automatically and momentarily to the released state during the insertion of a proximal end of a shaft or of a transmission device.

Each individual retaining device comprises in particular a bolt, a slide, a catch or a detent for form-fit retention or form-fit mechanical connection with the proximal end of a shaft or to the proximal end of a transmission device. The retaining device, or its bolt, slide, catch or detent, engages in particular in a corresponding recess at the proximal end of the shaft or of the transmission device. The bolt, slide, catch or detent is in particular movable in a direction perpendicular to the longitudinal axis of the proximal end of the shaft or of the transmission device. In a retaining or locking position, the bolt, slide, catch or detent retains the proximal end of the shaft or of the transmission device with a form fit on or in the retaining device. In a released position of the bolt, slide, catch or detent, the proximal end of the shaft or of the transmission device is freed and can be separated from the retaining device. The bolt, slide, catch or detent can be moved to the retaining position by a spring or by another elastic element.

Alternatively, a retaining device can be designed for the force-fit or friction-fit retention of a proximal end of a shaft or of a transmission device.

The manually activatable actuation device comprises in particular a push-button, a slide or a lever, which is manually movable in a direction parallel to the longitudinal axis of a shaft to be connected to the manipulation device, or perpendicular thereto. The actuation device is arranged on the manipulation device particularly in such a way that the actuation device can be easily activated with one hand, the hand holding the manipulation device, and in such a way that inadvertent activation is unlikely or impossible.

The coupling device couples the actuation device to the plurality of retaining devices particularly in such a way that, upon complete manual activation of the actuation device (for example by pressing a push-button or pulling a slide as far as a limit stop), all the retaining devices are released directly by the effect of the coupling device. The direct mechanical coupling of the plurality of retaining devices to the actuation device by means of the coupling device does not mean in particular that, as a result of the release of a first of the plurality of retaining devices, a change on the medical instrument is permitted only which effects or permits the release of a second of the plurality of retaining devices. In this, the present invention differs from the products sold by the applicant under the name "Clickline". However, this does not rule out the possibility that, in addition to the plurality of retaining devices on the manipulation device, one or more further retaining devices are provided which are released only indirectly in the stated sense. It is also possible that the plurality of retaining devices are not completely released simultaneously, in other words that the plurality of retaining devices (particularly in the event of slow activation of the actuation device) are released at least partially in succession.

In a manipulation device as described here, a first retaining device of the plurality of retaining devices is in particular designed to retain a proximal end of a shaft, and a second retaining device of the plurality of retaining devices is designed to retain a proximal end of a transmission device for transmitting at least either a force or a torque between the manipulation device and a tool at the distal end of the shaft.

Moreover, in the manipulation device, a third retaining device of the plurality of retaining devices is in particular designed to retain a proximal end of a further transmission device for transmitting at least either a force or a torque to a joint on the shaft.

The transmission device is in particular a transmission rod that transmits a force or a torque and that can be bendable and torsionally stiff. In particular, the further transmission device comprises a tubular or hose-like inner shaft, which is arranged coaxially in an annular space between the shaft or outer shaft, on the one hand, and the transmission rod, on the other hand. The inner shaft is in particular designed, in its entirety or in parts, to be rigid, flexible or able to be angled. The inner shaft and the transmission rod are displaceable in the longitudinal direction relative to the shaft or outer shaft, in particular independently of each other and with minimal play or friction, and are rotatable about the longitudinal direction or longitudinal axis.

The manipulation device permits simultaneous release, in the sense described above, of the mechanical connection between the proximal end of the outer shaft and the first retaining device assigned to the outer shaft, of the connection between the proximal end of the transmission rod and the second retaining device assigned to the transmission rod, and of the mechanical connection between the inner shaft and the third retaining device assigned to the inner shaft.

In a manipulation device as described here, a retaining device of the plurality of retaining devices, together with a proximal end of a shaft or of a transmission device retained by the retaining device, is movable relative to the actuation device, and the coupling device is designed to couple the actuation device to the movable retaining device, independently of the position of the movable retaining device relative to the actuation device.

In particular, several or all of the retaining devices of the plurality of retaining devices are each movable, together with the assigned proximal ends of a shaft or of a transmission device, relative to the actuation device. The mobility of a retaining device does not mean that movement of a retaining device or of a part of a retaining device which is provided and required for producing a connection with the assigned proximal end of a shaft or of a transmission device or for releasing this connection and for locking or unlocking the connection. Rather, this in each case means the mobility of a retaining device in the (translational or rotational) direction in which the retaining device is movable together with an assigned and mechanically connected proximal end of a shaft or of a transmission device. The position of a movable retaining device comprises its position with respect to translational and/or rotational degrees of freedom.

A manipulation device for mechanical connection with the proximal end of a shaft, for forming a medical instrument, comprises a retaining device for releasably retaining the proximal end of a shaft or the proximal end of a transmission device for transmitting at least either a force or a torque, a manually activatable actuation device, and a coupling device for mechanically coupling the actuation device to the retaining device, in such a way that a manual activation of the actuation device causes a release of the retaining device, wherein the retaining device, together with a proximal end of a shaft or of a transmission device retained by the retaining device, is movable relative to the actuation device, and wherein the coupling device is designed to couple the actuation device to the movable retaining device, independently of the position of the movable retaining device relative to the actuation device.

The above observations apply accordingly as regards the medical instrument for which the manipulation device is provided, as regards the design of the retaining device, its function and effect, as regards the actuation device, and as regards the coupling device and its function and effect.

In a manipulation device with a movable retaining device, as described here, the movable retaining device, together with a proximal end of a shaft or of a transmission device retained by the movable retaining device, is in particular displaceable relative to the actuation device parallel to the longitudinal axis of the shaft or of the transmission device.

In particular, the movable retaining device, together with a proximal end of a transmission rod or of an inner shaft retained by the movable retaining device, is displaceable parallel to the longitudinal axis thereof, for example in order to permit transfer of a force for opening or closing a jaw part at the distal end of the shaft or for moving the shaft at an angle at a joint.

In a manipulation device with a movable retaining device, as described here, the movable retaining device, together with a proximal end of a shaft or of a transmission device retained by the movable retaining device, is in particular rotatable relative to the actuation device about a longitudinal axis of the shaft or of the transmission device.

For example, the movable retaining device, together with a proximal end of a transmission rod retained by the movable retaining device, is rotatable in order to permit transfer of a torque and of a rotation movement to a tool at the distal end of the shaft. For example, the movable retaining device, together with the proximal end of an inner shaft, is rotatable in order to permit a rotation of a joint, where the shaft can be set at an angle, and a pivot axis defined by the joint, about a longitudinal axis of the shaft.

In a manipulation device as described here, the actuation device for the activation is in particular manually displaceable in a direction parallel to the longitudinal axis of a shaft connected to the manipulation device.

The actuation device is designed, for example, in the form of a cylindrical sleeve that can be gripped with two fingers and pulled in the proximal direction, in order to release the retaining device or the retaining devices.

In a manipulation device as described here, the coupling device comprises in particular a coupling element, which is displaceable in a first direction of movement, and a slide surface with an area that is not parallel to the first direction of movement, in order to convert a displacement of the coupling element in the first direction of movement into a movement of a bolt in a second direction of movement, which is different than the first direction of movement.

The coupling element is in particular identical or partially identical or rigidly connected to the actuation device or is coupled to the actuation device in such a way that, upon manual activation of the actuation device, it is moved in the first direction of movement. The first direction of movement is in particular parallel to the longitudinal axis of a shaft connected to the manipulation device.

On account of its being non-parallel or inclined with respect to the first direction of movement, the slide surface has a function similar to that known from a wedge. The slide surface can be designed as a conical surface or can comprise a conical area in order to act, independently of its angle position, with respect to a rotation about the axis of symmetry of the conical surface. The slide surface can be provided on the coupling element. A displacement of the coupling element in the first direction of movement can be converted directly or indirectly into a movement of a bolt in the second direction of movement. Direct conversion can be provided, for example, if the bolt and the coupling element bear on each other at the slide surface, in which case the slide surface can be provided on the bolt or on the coupling element. Indirect conversion can be provided by further elements between the slide surface and the bolt.

In a manipulation device as described here, the bolt bears in particular directly on the slide surface. For example, the coupling element is identical or partially identical to the sleeve-shaped actuation device. The outside of the actuation device is designed, through its arrangement and configuration (for example a ribbed surface) for manual activation. The inside of the sleeve-shaped actuation device has a conical slide surface, or a slide surface with a conical area on which an end of the bolt bears. The axis of symmetry of the conical slide surface, or of the conical area of the slide surface, is in particular identical to the longitudinal axis of the shaft. A manual movement of the actuation device or of the coupling element parallel to the axis of symmetry of the conical slide surface can cause a radial movement of the bolt with respect to the longitudinal axis of the shaft.

A manipulation device with a coupling element, as described here, has in particular a further coupling element, which bears on the coupling element and is movable in the second direction of movement, wherein the bolt is mechanically coupled to the further coupling element.

The slide surface is in particular provided on the coupling element and bears on the further coupling element, or the slide surface is provided on the further coupling element and bears on the coupling element. Moreover, both the coupling element and also the further coupling element can each have a slide surface with an area that is not parallel to the first direction of movement or that is inclined with respect to the first direction of movement, which slide surfaces bear on each other. The further coupling element extends in particular in the longitudinal direction of a shaft to be connected to the manipulation device (for example in the form of a plate-shaped structural part) and bears on one or more bolts spaced apart in the longitudinal direction of one or more retaining devices. Such a design of the further coupling element can permit a coupling of the actuation device to one or more longitudinally displaceable retaining devices independently of their position or positions.

In a manipulation device with a further coupling element, as described here, either the further coupling element can in particular have the slide surface, or the slide surface can bear slidingly on the further coupling element.

In a manipulation device with a movable retaining device and with a further coupling element, as described here, the movable retaining device is in particular displaceable, together with a proximal end of a shaft or of a transmission device retained by the movable retaining device, relative to the actuation device parallel to the longitudinal axis of the shaft or of the transmission device, and the further coupling element and the movable retaining device are designed to be mechanically coupled to each other in all positions of the movable retaining device.

In particular, the further coupling element has a support surface, which is parallel to the longitudinal axis of a proximal end of a shaft or a transmission device retained by the movable retaining device, and on which a bolt of the movable retaining device bears.

In particular, in a manipulation device as described here, the second direction of movement is at least either perpendicular to the first direction of movement or perpendicular to the longitudinal axis of a shaft connected to the manipulation device.

A medical instrument comprises a manipulation device as described here.

BRIEF DESCRIPTION OF THE DRAWINGS

Embodiments are explained in more detail below with reference to the attached figures, in which.

DETAILED DESCRIPTION OF THE INVENTION

Figure 1:
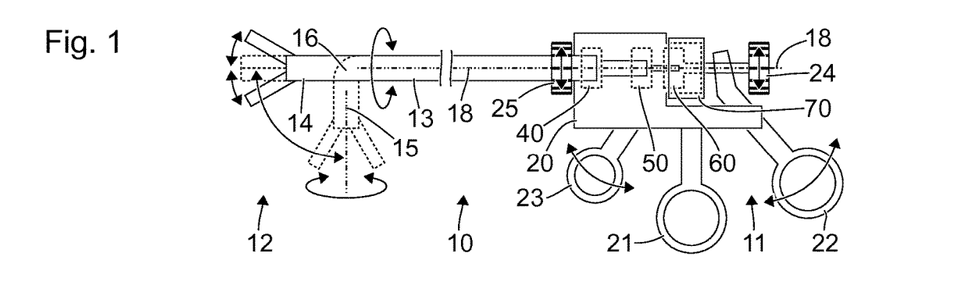
FIG. 1 shows a schematic view of a medical instrument.

FIG. 1 shows a schematic view of a medical instrument 10 with a proximal end 11 and a distal end 12. A shaft, which comprises an outer shaft 13, an inner shaft and a transmission rod, extends as far as the distal end 12 of the medical instrument 10. At the distal end of the outer shaft 13, a tool 14 is provided which is designed, for example, as a grasping or cutting tool with two movable jaw parts. A joint 16 is provided proximally of the tool 14 on the outer shaft 13.

A number of arrows and dashed contours indicate degrees of mobility or freedom. In particular, the two jaw parts of the tool 14 can be opened, i.e. moved away from each other, and closed, i.e. moved toward each other (pivot axes of the jaw parts perpendicular to the plane of the drawing of FIG. 1); the tool 14 with its jaw parts can be rotated about its longitudinal axis 15; the tool 14, with the longitudinal axis 15 thereof, can be pivoted about a pivot axis defined by the joint 16; the outer shaft 13, and with it the joint 16, the pivot axis defined by the joint 16, and the tool 14, can be rotated about the longitudinal axis 18 of the outer shaft 13.

At the proximal end 11, the medical instrument 10 has a manipulation device 20 with a stationary grip part 21, a first movable grip part 22 and a second movable grip part 23. In FIG. 1, arrows indicate that the first movable grip part 22 and the second movable grip part 23 are each pivotable about an assigned pivot axis perpendicular to the plane of the drawing of FIG. 1. Moreover, the manipulation device 20 has a first rotary wheel 24 and a second rotary wheel 25 which (as indicated by arrows) are each rotatable about the longitudinal axis 18 of the outer shaft 13. The first rotary wheel 24 is arranged on a proximal side of the manipulation device 20, and the second rotary wheel 25 on a distal side. The arrangement and design of the stationary grip part 21, of the movable grip parts 22, 23 and of the rotary wheels 24, 25 may differ markedly from FIG. 1 for purposes of improved ergonomics.

The movable grip parts 22, 23 and the rotary wheels 24, 25 are coupled to the outer shaft 13, to the tool 14 and the jaw parts thereof, and to the joint 16, in such a way that the abovementioned degrees of freedom can be controlled in particular independently of one another and in particular simultaneously or in alternation. For example, the second rotary wheel 25 is coupled to the outer shaft (in particular connected to the outer shaft 13 rigidly, releasably or non-releasably), in order to permit a rotation of the outer shaft 13 about its longitudinal axis 18.

The second movable grip part 23 is coupled to a first retaining device 40 and to a second retaining device 50 by means of a coupling device not shown in FIG. 1. The second movable grip part 23 is coupled to the outer shaft 13 via the first retaining device 40 and to an inner shaft via the second retaining device 50. The outer shaft 13 and the inner shaft are coupled to the joint 16 near the distal end of the outer shaft 13, in such a way that a relative movement of the outer shaft 13 and of the inner shaft parallel to the longitudinal axis 18, brought about by means of the second movable grip part 23, controls an angled movement at the joint 16.

The first movable grip part 22 and the first rotary wheel 24 are coupled by means of a third retaining device 60 to a transmission rod, and are coupled by means of the transmission rod to the tool 14, and in particular to the pivotable jaw parts thereof. By means of a pivoting movement of the first movable grip part 22, it is possible to control a translation movement of the transmission rod parallel to the longitudinal axis 18 and an opening or closing movement of the jaw parts of the tool 14. By rotation of the first rotary wheel 24, it is possible to control a rotation of the transmission rod about the longitudinal axis 18 and a rotation of the tool 14 about its longitudinal axis 15.

Alternatively, another assignment of the movable grip parts 22, 23 and of the rotary wheels 24, 25 to the degrees of freedom is possible. To control the kinking of the distal end of the outer shaft 13 at the joint 16, it is possible, for example, for the second movable grip part 23 to be replaced by a further rotary wheel. Moreover, several degrees of freedom can be controlled by one actuation device. For example, by means of an axially displaceable rotary wheel, it is possible, depending on the axial position thereof, to control either the kinking of the distal end of the outer shaft 13 at the joint 16 or the rotation of the tool 14 about the longitudinal axis 15 thereof.

The medical instrument 10 can be dismantled. In particular, the outer shaft 13 can be separated, together with the inner shaft and the transmission rod, from the manipulation device 20. The retaining devices 40, 50, 60 are designed to releasably retain the proximal ends of the outer shaft 13, of the inner shaft and of the transmission rod or to be mechanically connected to these ends in a releasable manner. Moreover, it is possible for the tool 14, together with the transmission rod, and for the joint 16, together with the inner shaft, to be separated from the outer shaft 13 and/or removed distally from the outer shaft 13.

An actuation device 70 is operatively coupled to the retaining devices 40, 50, 60. By activating the actuation device 70, in particular by manually moving the actuation device 70 parallel to the longitudinal axis 18 in the proximal direction, it is possible to release all the connections between the retaining devices 40, 50, 60 and the respectively assigned proximal end of the outer shaft 13, of the inner shaft and of the transmission rod. During or after activation of the actuation device 70, the proximal end of the outer shaft 13, together with the proximal end of the inner shaft and the proximal end of the transmission rod, can be pulled distally out of the manipulation device 20 or can be ejected distally out of the manipulation device 20 by a spring force.

The pivotable grip parts 22, 23 and the rotary wheels 24, 25 are mechanically and operatively coupled to the retaining devices 40, 50, 60, in such a way that the retaining devices 40, 50, 60, together with the respectively assigned proximal end of the outer shaft 13 and inner shaft or of the transmission rod, can be displaced parallel to the longitudinal axis 18 and/or can be rotated about the longitudinal axis 18. The actuation device 70 is mechanically and operatively coupled to the retaining devices 40, 50, 60, in such a way that a manual activation of the actuation device 70 causes a release of the mechanical connection between the retaining devices 40, 50, 60 and the respectively assigned proximal end of the outer shaft 13 or of the inner shaft or of the transmission rod. The mechanical coupling between the actuation device 70 on the one hand and the retaining devices 40, 50, 60 on the other hand is described below with reference to FIGS. 2 to 7, specifically independently of the mechanical coupling of the pivotable grip parts 22, 23 and rotary wheels 24, 25 to the retaining devices 40, 50, 60.

Figure 2:
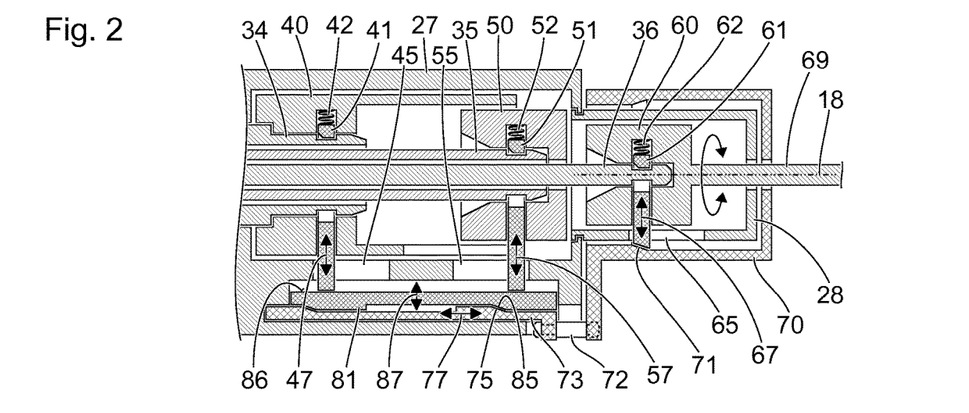
FIG. 2 shows a schematic sectional view of a part of a manipulation device.

FIG. 2 shows a schematic sectional view of a part of a manipulation device, in particular of the manipulation device 20 described above with reference to FIG. 1. The sectional plane shown in FIG. 2 contains the longitudinal axis 18 of the outer shaft (cf. FIG. 1). The part of the manipulation device shown in FIG. 2 comprises the retaining devices 40, 50, 60, the actuation device 70 and the mechanical coupling, which have already been described above with reference to FIG. 1. FIG. 2 does not show the mechanical coupling of the retaining devices 40, 50, 60 to movable grip parts and rotary wheels (not shown in FIG. 2). The retaining devices 40, 50, 60 can be coupled to movable grip parts and rotary wheels which, in terms of their arrangement and design, differ from those described above with reference to FIG. 1.

FIG. 2 shows a partial area of a stationary housing part 27 and of a rotatable housing part 28 of the manipulation device. The rotatable housing part 28 is connected to the stationary housing part 27 with a form fit, in such a way that it is rotatable relative to the latter about the longitudinal axis 18. The first retaining device 40 and the second retaining device 50 are arranged in the stationary housing part 27, and the third retaining device 60 is arranged in the rotatable housing part 28. The proximal end 34 of an outer shaft, the proximal end 35 of an inner shaft and the proximal end 36 of a transmission rod protrude into the manipulation device from the distal side (the left-hand side in FIGS. 1 and 2). The transmission rod is arranged coaxially in the substantially tubular inner shaft. The transmission rod and the inner shaft are arranged coaxially in the substantially tubular outer shaft. The longitudinal axis 18 is therefore at the same time the longitudinal axis of the proximal end 34 of the outer shaft, of the proximal end 35 of the inner shaft, and of the proximal end 36 of the transmission rod. In particular, the proximal end 34 of the outer shaft, the proximal end 35 of the inner shaft and the proximal end 36 of the transmission rod are each substantially rotationally symmetrical with respect to the longitudinal axis 18. The outer shaft, the inner shaft and the transmission rod can be curved distally of the manipulation device, with the inner shaft and the transmission rod in particular being flexible.

The retaining devices 40, 50, 60 each comprise a recess, which is not provided with a reference sign in FIG. 2 and of which the shape is adapted to the shape of the proximal end 34 of the outer shaft or to the shape of the proximal end 35 of the inner shaft, or to proximal end 36 of the transmission rod. These recesses extend substantially parallel to the longitudinal axis 18 and can widen in a funnel shape in the distal direction, as is indicated for the second retaining device 50 and the third retaining device 60 in FIG. 2. The recesses in the retaining devices 40, 50, 60 are designed in particular by step-shaped shoulders or end walls, such that they each form a proximal abutment for the proximal end 34 of the outer shaft, for the proximal end 35 of the inner shaft and for the proximal end 36 of the transmission rod. This allows a distally directed force (thrust) to be transferred from a retaining device 40, 50, 60 to the assigned proximal end 34, 35, 36 of the outer shaft, inner shaft and transmission rod.

The cross sections of the proximal end 34 of the outer shaft, of the proximal end 35 of the inner shaft and of the proximal end 36 of the transmission rod, and the corresponding cross sections of the recesses in the assigned retaining devices 40, 50, 60, can each be circular in planes perpendicular to the longitudinal axis 18 or can have a shape that is not rotationally symmetrical with respect to the longitudinal axis 18. In the case of corresponding non-rotationally symmetrical cross sections, a torque can be transferred.

In particular, the proximal end 34 of the outer shaft and the corresponding recess in the first retaining device 40, and the proximal end 35 of the inner shaft and the corresponding recess in the second retaining device 50, are each rotationally symmetrical with respect to the longitudinal axis 18. Therefore, the proximal end 34 of the outer shaft can be freely rotated relative to the first retaining device 40, and the proximal end 35 of the inner shaft can be freely rotated relative to the second retaining device 50 about the longitudinal axis 18. The proximal end 36 of the transmission rod and the corresponding recess of the assigned third retaining device 60 are in particular designed to be non-rotationally symmetrical with respect to the longitudinal axis 18, so as to permit the transfer of a torque between the third retaining device 60 and the proximal end 36 of the transmission rod.

In the first retaining device 40, there is a bolt 41 which is displaceable in a direction of movement 47 perpendicular to the longitudinal axis 18 and is pushed by a spring 42 into the position shown in FIG. 2, in which the bolt 41 engages in a groove at the proximal end 34 of the outer shaft. An end of the bolt 41 facing away from the spring 42 engages through a slit 45 in the stationary housing part 27. In the second retaining device 50, there is a bolt 51 which is displaceable in a direction of movement 57 perpendicular to the longitudinal axis 18 and is pushed by a spring 52 into the position shown in FIG. 2, in which the bolt 51 engages in a groove at the proximal end 35 of the inner shaft. An end of the bolt 51 facing away from the spring 52 engages through a slit 55 in the stationary housing part 27. In the third retaining device 60, there is a bolt 61 which is displaceable in a direction of movement 67 perpendicular to the longitudinal axis 18 and is pushed by a spring 62 into the position shown in FIG. 2, in which the bolt 61 engages in a groove at the proximal end 36 of the transmission rod. An end of the bolt 61 facing away from the spring 62 engages through a slit 65. Each bolt 41, 51, 61 is designed in particular as a plate with a hole or continuous bore through which the proximal end 34 of the outer shaft, the proximal end 35 of the inner shaft or the proximal end 36 of the transmission rod engages.

The actuation device 70 surrounds the rotatable housing part 28 substantially in a beaker shape. The outside of the actuation device 70 can be ribbed (not shown in FIG. 2), so that it is easy for the actuation device 70 to be gripped by hand and pulled in the proximal direction. On the inside, the actuation device 70 has a slide surface 71 with a conical area. The end of the bolt 61, of the third retaining device 60, engaging through the slit 65 in the rotatable housing part 27 bears on the slide surface 71.

The actuation device 70 is rigidly connected to a carriage 73 by means of a connecting rod 72, which carriage 73 is mainly arranged inside the stationary housing part 27. The connecting rod 72 is connected to the actuation device 70 and to the carriage 73 in each case by material-to-material bonding, with a form fit and/or with a frictional fit. The actuation device 70 and the carriage 73 are jointly movable or displaceable in a direction of movement 77 parallel to the longitudinal axis 18. A spring (not shown in FIG. 2) or another elastic element can be provided in order to push or pull the actuation device 70 and the carriage 73 to the position shown in FIG. 2.

A lifting plate 81 is arranged between the carriage 73, on the one hand, and the first retaining device 40 and second retaining device 50, on the other hand. A slide surface 75 on the carriage 73 bears on a slide surface 85 on the lifting plate 81. The slide surface 75 on the carriage 73 and the slide surface 85 on the lifting plate 81 each have an area that is not parallel to the direction of movement 77 or that is inclined relative to the direction of movement 77 of the carriage 73. In the first retaining device 40 and the second retaining device 50, the ends of the bolts 41, 51 facing away from the springs 42, 52 bear on a support surface 86 provided on the opposite side of the lifting plate 81 from the slide surface 85. The lifting plate 81 is guided in the stationary housing part 27 so as to be movable in a direction of movement 87 perpendicular to the longitudinal axis 18 and to the direction of movement 77 of the carriage 73, and also parallel to the directions of movement 47, 57 of the bolts 41, 51 of the first retaining device 40 and of the second retaining device 50.

Figure 3:
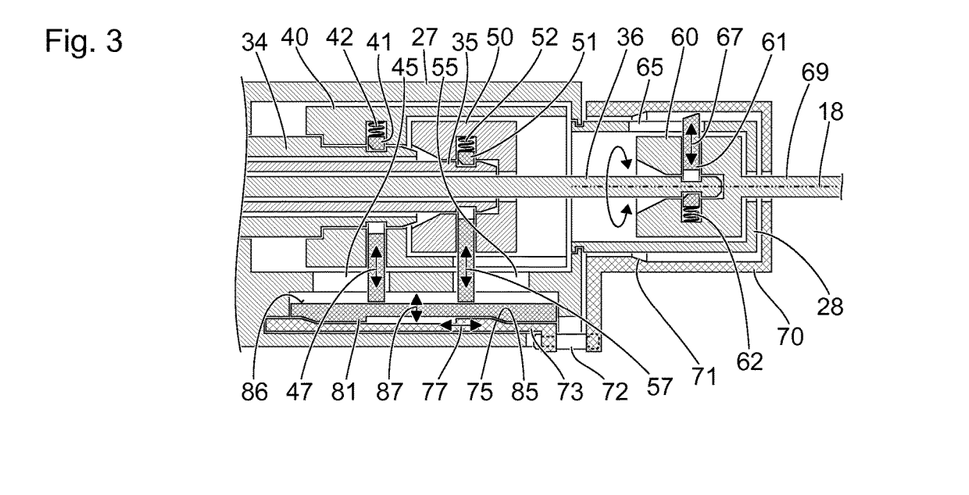
FIG. 3 shows a further schematic sectional view of the part of the manipulation device from FIG. 2.

FIG. 3 shows a further schematic view of the part of a manipulation device shown in FIG. 2, corresponding to FIG. 2 particularly in terms of the sectional plane. In the example shown in FIGS. 2 and 3, the first retaining device 40 together with the proximal end 34 of the outer shaft, the second retaining device 50 together with the proximal end 35 of the inner shaft, and the third retaining device 60 together with the proximal end 36 of the transmission rod, are each displaceable parallel to the longitudinal axis 18. Moreover, in the example shown in FIGS. 2 and 3, the third retaining device 60 together with the transmission rod is rotatable about the longitudinal axis 18. The view in FIG. 3 differs from the view in FIG. 2 in that the first retaining device 40 together with the proximal end 34 of the outer shaft has been displaced from the distal position shown in FIG. 2 to a proximal position; the second retaining device 50 together with the proximal end 35 of the inner shaft has been displaced from the proximal position shown in FIG. 2 to a distal position; and the third retaining device 60 together with the proximal end 36 of the transmission rod has been displaced from the distal position shown in FIG. 2 to a proximal position. In addition, the third retaining device 60, together with the rotatable housing part 28 and the transmission rod, is rotated 180 degrees about the longitudinal axis 18 relative to the position shown in FIG. 2. It will be seen that, in the positions of the retaining devices 40, 50, 60 shown in FIG. 3, the ends of the bolts 41, 51, 61 facing away from the springs 42, 52, 62 also bear on the support surface 85 of the lifting plate 81 and on the slide surface 71 of the actuation device 70.

As has already been mentioned, FIGS. 1 to 3 do not show the operative mechanical coupling between the retaining devices 40, 50, 60, on the one hand, and the movable grip parts 22, 23 and rotary wheels 24, 25, on the other hand. FIGS. 2 and 3 indicate, merely by way of example, a stem 69 of which the distal end is rigidly connected to the third retaining device 60. In the example shown in FIG. 1, the proximal end (not shown in FIGS. 2 and 3) can be coupled to the first movable grip part 22 and to the first rotary wheel 24. The first retaining device 40 and the second retaining device 50 can be movable independently of each other, or they can be coupled to each other, for example via opposing threads, such that they are always moved in opposite directions.

Figure 4:
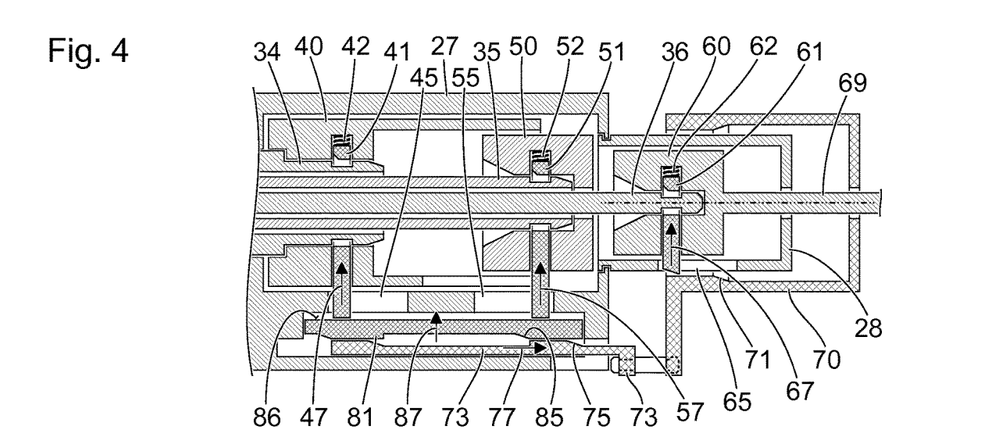
FIG. 4 shows a further schematic sectional view of the part of the manipulation device from FIGS. 2 and 3.
Figure 5:
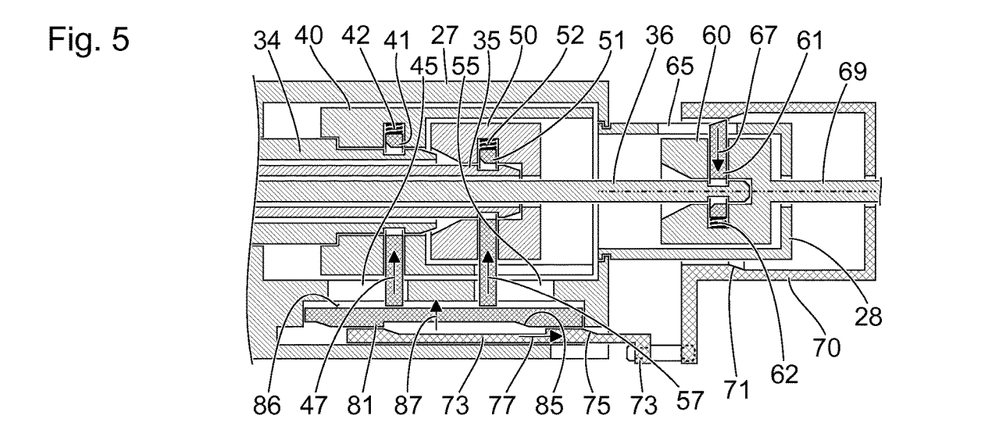
FIG. 5 shows a further schematic sectional view of the part of the manipulation device from FIGS. 2 to 4.

FIGS. 4 and 5 each show a further schematic sectional view of the example from FIGS. 2 and 3. The views in FIGS. 4 and 5 correspond to FIGS. 2 and 3 in particular in terms of the sectional planes depicted. In the view in FIG. 4, the first retaining device 40 and the proximal end 34 of the outer shaft assume the distal positions also shown in FIG. 2, and, in the view in FIG. 5, they assume the proximal positions also shown in FIG. 3. In the view in FIG. 4, the second retaining device 50 and the proximal end 35 of the inner shaft assume the proximal positions shown in FIG. 2, and, in FIG. 5, they assume the distal positions shown in FIG. 3. In the view in FIG. 4, the third retaining device 60 and the proximal end 36 of the transmission rod assume the positions shown in FIG. 2, and, in the view in FIG. 5, they assume the positions shown in FIG. 3. To this extent, FIG. 4 corresponds to FIG. 2, and FIG. 5 corresponds to FIG. 3.

The views in FIGS. 4 and 5 differ from the views in FIGS. 2 and 3 in terms of the fact that the actuation device 70 is activated, that is to say is displaced in the proximal direction. It will be seen in FIGS. 4 and 5 that, by means of the connecting rod 72, this displacement causes a corresponding displacement of the carriage 73 and, by means of the wedge effect of the inclined sections of the slide surfaces 75, 85, causes a displacement of the lifting plate 81 in the direction of movement 87 toward the first retaining device 40 and the second retaining device 50. This displacement of the lifting plate 81 causes a corresponding displacement of the bolts 41, 51 counter to the forces of the springs 42, 52, since the ends of the bolts 41, 51 facing away from the springs 42, 52 bear on the support surface 86 of the lifting plate 81. The wedge effect of the conical area of the slide surface 71 on the inside of the actuation device 70 causes a corresponding displacement of the bolt 61 of the third retaining device 60 counter to the force of the spring 62. The displacement of the actuation device 70 in the proximal direction, to the positions shown in FIGS. 4 and 5, thus causes a displacement of the bolts 41, 51, 61 of the retaining devices 40, 50, 60 to the positions shown in FIGS. 4 and 5.

In the positions shown in FIGS. 4 and 5, the bolts 41, 51, 61 no longer engage in the grooves at the proximal end 34 of the outer shaft and at the proximal end 35 of the inner shaft and at the proximal end 36 of the transmission rod. The mechanical connections are thus released or unlocked, and the proximal end 34 of the outer shaft, the proximal end 35 of the inner shaft and the proximal end 36 of the transmission rod are freed and can be pulled in the distal direction out of the manipulation device. Comparing FIGS. 4 and 5, it will be seen that, by means of the illustrated displacement of the actuation device 70 in the proximal direction, the mechanical connection of the first retaining device 40 to the proximal end 34 of the outer shaft, the mechanical connection of the second retaining device 50 to the proximal end 35 of the inner shaft, and the mechanical connection of the third retaining device 60 to the proximal end 36 of the transmission rod are released substantially at the same time and independently of the positions of the retaining devices 40, 50, 60.

Looking at FIGS. 2 to 5, it will be seen that the slide surface 71 on the actuation device 70, the connecting rod 72, the carriage 73 and the lifting plate 81 form a coupling device for mechanically coupling the actuation device 70 to the bolts 41, 51, 61 of the retaining devices 40, 50, 60.

Figure 6:
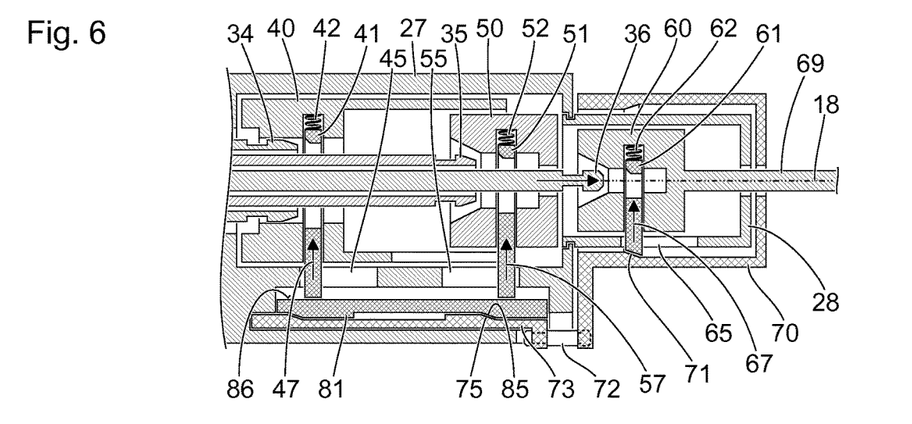
FIG. 6 shows a further schematic sectional view of the part of the manipulation device from FIGS. 2 to 5.

FIG. 6 shows a further schematic sectional view of the part of a manipulation device also shown in FIGS. 2 to 5. The view in FIG. 6 corresponds to the views in FIGS. 2 to 5 in particular in terms of the sectional plane. The retaining devices 40, 50, 60, the actuation device 70, the carriage 73 and the lifting plate 81 assume the positions already shown in FIG. 2. The view in FIG. 6 differs from the view in FIG. 2 in terms of the fact that the proximal end 34 of the outer shaft, the proximal end 35 of the inner shaft and the proximal end 36 of the transmission rod are not retained by the retaining devices 40, 50, 60. The proximal end 34 of the outer shaft, the proximal end 35 of the inner shaft and the proximal end 36 of the transmission rod are instead shown in distally displaced positions.

In the state shown in FIG. 6, the bolts 41, 51, 61, on account of the action of the springs 42, 52, 62, assume positions corresponding to the retaining or locking positions shown in FIGS. 2 and 3.

By moving the proximal end 34 of the outer shaft, the proximal end 35 of the inner shaft and the proximal end 36 of the transmission rod in the proximal direction, they can be received by the retaining devices 40, 50, 60 and locked in the retaining devices 40, 50, 60. No activation of the actuation device 70 is needed for this purpose. Slide surfaces, inclined with respect to the longitudinal axis 18, on the proximal end 34 of the outer shaft, on the proximal end 35 of the inner shaft, on the proximal end 36 of the transmission rod and on the bolts 41, 51, 61 of the retaining devices 40, 60, 60, cause a momentary displacement of the bolts 41, 51, 61 in the directions of movement 47, 57, 67 counter to the forces of the springs 42, 52, 62. Without activation of the actuation device 70, the bolts 41, 51, 61 momentarily assume their release positions, shown in FIGS. 3 and 5, until the bolts 41, 51, 61, as shown in FIG. 2, engage in the grooves at the proximal end 34 of the outer shaft, at the proximal end 35 of the inner shaft and at the proximal end 36 of the transmission rod and retain these with a form fit. In the first retaining device 40 and the second retaining device 50, the ends of the bolts 41, 51 facing away from the springs 42, 52 are momentarily lifted from the support surface 86 on the lifting plate 81.

Figure 7:
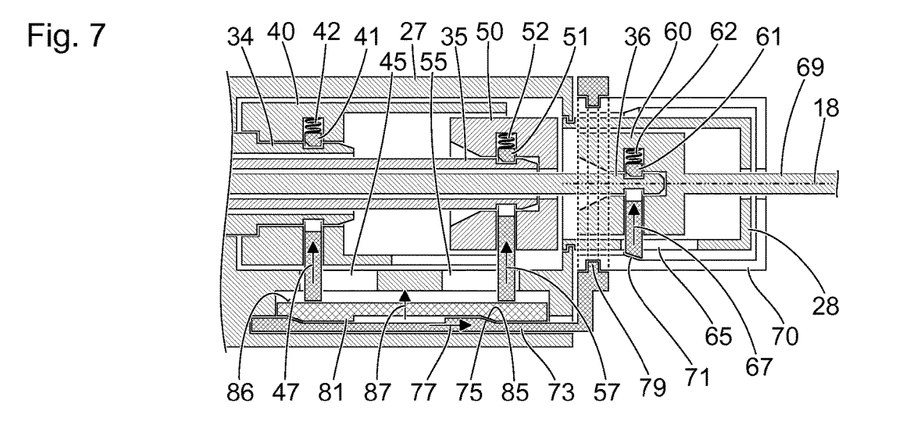
FIG. 7 shows a schematic sectional view of a part of a further manipulation device.

FIG. 7 shows a schematic sectional view of a part of a further illustrative embodiment of a retaining device which, in terms of certain features, is similar to the illustrative embodiment of FIGS. 2 to 6. The view in FIG. 7 corresponds to the views of FIGS. 2 to 6, in particular in terms of the sectional plane.

The illustrative embodiment shown in FIG. 7 is similar to the illustrative embodiment in FIGS. 2 to 6, in particular in terms of the design of the retaining devices 40, 50, 60, the carriage 73 and the lifting plate 81. The illustrative embodiment in FIG. 3 differs from the illustrative embodiment in FIGS. 2 to 6 particularly in that the actuation device 70 is rotatable relative to the carriage 73 about the longitudinal axis 18. For this purpose, a rotary bearing 79 is provided between the actuation device 70 and the carriage 73 and connects both of these with a form fit and such that they are rotatable relative to each other about the longitudinal axis 18.

In FIG. 7, as in the illustrative embodiment in FIGS. 2 to 6, a slide surface 71 with a conical section is shown on the inside of the actuation device 70. Since the actuation device 70 is rotatable relative to the carriage 73 about the longitudinal axis 18, the actuation device 70 can be coupled to the rotatable housing part 28 and to the third retaining device 60 via features not shown in FIG. 7, such that a rotation of the actuation device 70 about the longitudinal axis 18 causes a corresponding rotation of the third retaining device 60, and therefore also of the proximal end 36 of the transmission rod retained in the third retaining device 60, about the longitudinal axis 18. In this case, in a departure from the view in FIG. 7, it is possible, instead of a conical section, merely to provide a strip-shaped, ramp-shaped section on the slide surface 71 on the actuation device 70.

REFERENCE SIGNS 10 medical instrument
11 proximal end of the medical instrument 10
12 distal end of the medical instrument 10
13 outer shaft of the medical instrument 10
14 tool
15 longitudinal axis of the tool 14
16 joint on the outer shaft 13
18 longitudinal axis of the outer shaft 13
20 manipulation device of the medical instrument 10
21 stationary grip part of the manipulation device 20
22 first movable grip part on the manipulation device 20
23 second movable grip part on the manipulation device 20
24 first rotary wheel on the manipulation device 20
25 second rotary wheel on the manipulation device 20
27 stationary housing part of the manipulation device 20
28 rotatable housing part of the manipulation device 20
34 proximal end of the outer shaft 13
35 inner shaft, proximal end of the inner shaft
36 transmission rod, proximal end of the transmission rod
40 first retaining device for proximal end 34 of the outer shaft
41 bolt of the first retaining device 40
42 spring on the bolt 41
45 slit in the stationary housing part 27 for bolt 41
47 direction of movement of the bolt 41
50 second retaining device for proximal end of the inner shaft 35
51 bolt of the second retaining device 50
52 spring on the bolt 51
55 slit in the stationary housing part 27 for bolt 51
57 direction of movement of the bolt 51
60 third retaining device for proximal end of the transmission rod 36
61 bolt of the third retaining device 60
62 spring on the bolt 61
65 slit in the rotatable housing part 27 for bolt 61
67 direction of movement of the bolt 61
69 stem on the third retaining device 60
70 actuation device for unlocking
71 slide surface on the actuation device 70
72 connecting rod
73 carriage
75 slide surface on carriage 73
77 direction of movement of the carriage 73

79 rotary bearing for rotatable part 78
81 lifting plate
85 slide surface on the lifting plate 81
86 support surface of the lifting plate 81
87 direction of movement of the lifting plate 81

The invention claimed is:

1. A manipulation device for mechanical connection with a proximal end of a shaft, for forming a medical instrument, the manipulation device comprising:
 a plurality of retaining devices, wherein each one of the plurality of retaining devices is configured to releasably retain a proximal end of a shaft or a proximal end of a transmission device to transmit at least one of a force and a torque in the shaft;
 a manually activatable actuation device; and
 a coupling device configured to mechanically couple the actuation device to the plurality of retaining devices, in such a way that a manual activation of the actuation device causes a release of the plurality of retaining devices
 wherein a movable retaining device of the plurality of retaining devices is movable relative to the actuation device;
 wherein the coupling device is configured to couple the actuation device to the movable retaining device, independently of a position of the movable retaining device relative to the actuation device; and
 wherein the movable retaining device is movable relative to the actuation device in a direction parallel to a longitudinal axis of the shaft or of the transmission device.

2. The manipulation device according to claim 1, wherein a first retaining device of the plurality of retaining devices is configured to retain a proximal end of a shaft; and
 wherein a second retaining device of the plurality of retaining devices is configured to retain a proximal end of a transmission device for transmitting at least either a force or a torque between the manipulation device and a tool at a distal end of the shaft.

3. The manipulation device according to claim 1, wherein the movable retaining device is rotatable relative to the actuation device about the longitudinal axis of the shaft or of the transmission device.

4. The manipulation device according to claim 1, wherein the actuation device is manually displaceable in a direction parallel to the longitudinal axis of the shaft, which is connected to the manipulation device.

5. The manipulation device according to claim 1, wherein the coupling device includes:
 a coupling element, which is displaceable in a first direction of movement; and
 a slide surface with an area that is not parallel to the first direction of movement, in order to convert a displacement of the coupling element in the first direction of movement into a movement of a bolt in a second direction of movement, which is different than the first direction of movement.

6. The manipulation device according to claim 5, wherein the bolt bears on the slide surface.

7. The manipulation device according to claim 5, further comprising:
 a further coupling element, which bears on the coupling element and is movable in the second direction of movement, wherein the bolt is mechanically coupled to the further coupling element.

8. The manipulation device according to claim 7, wherein either the further coupling element has the slide surface, or the slide surface bears slidingly on the further coupling element.

9. The manipulation device according to claim 7, wherein the further coupling element has a support surface, which is parallel to the longitudinal axis of a proximal end of a shaft or a transmission device retained by the movable retaining device, and on which a bolt of the movable retaining device bears.

10. The manipulation device according to claim 5, wherein the second direction of movement is at least either perpendicular to the first direction of movement or perpendicular to the longitudinal axis of a shaft connected to the manipulation device.

11. A manipulation device for mechanical connection with a proximal end of a shaft, for forming a medical instrument, the manipulation device comprising:
 a retaining device configured to releasably retain a proximal end of a shaft or a proximal end of a transmission device to transmit at least one of a force and a torque in the shaft;
 a manually activatable actuation device; and
 a coupling device configured to mechanically couple the actuation device to the retaining device, in such a way that a manual activation of the actuation device causes a release of the retaining device;
 wherein the retaining device is movable relative to the actuation device;
 wherein the coupling device is configured to couple the actuation device to the retaining device, independently of a position of the retaining device relative to the actuation device; and
 wherein the retaining device is movable relative to the actuation device in a direction parallel to a longitudinal axis of the shaft or of the transmission device.

12. A medical instrument, comprising:
 a manipulation device for mechanical connection with a proximal end of a shaft, for forming a medical instrument, the manipulation device including:
  a plurality of retaining devices, wherein each one of the plurality of retaining devices is configured to releasably retain a proximal end of a shaft or a proximal end of a transmission device to transmit at least one of a force and a torque in the shaft;
  a manually activatable actuation device; and
  a coupling device configured to mechanically couple the actuation device to the plurality of retaining devices, in such a way that a manual activation of the actuation device causes a release of the plurality of retaining devices
  wherein a movable retaining device of the plurality of retaining devices is movable relative to the actuation device;
  wherein the coupling device is configured to couple the actuation device to the movable retaining device, independently of a position of the movable retaining device relative to the actuation device; and
 wherein the movable retaining device is movable relative to the actuation device in a direction parallel to a longitudinal axis of the shaft or of the transmission device.

* * * * *